United States Patent
Rosenbrand et al.

(10) Patent No.: US 6,433,217 B1
(45) Date of Patent: Aug. 13, 2002

(54) PROCESS FOR THE PREPARATION OF GLYCIDYLESTERS OF BRANCHED CARBOXYLIC ACIDS

(76) Inventors: Gerrit Gerardus Rosenbrand; Hendrik Stichter; Denis Marie Charles Heymans, all of Badhuisweg 3, 1031 CM, Amsterdam (NL)

( * ) Notice: Subject to any disclaimer, the term of this patent is extended or adjusted under 35 U.S.C. 154(b) by 0 days.

(21) Appl. No.: 09/404,527

(22) Filed: Sep. 23, 1999

(30) Foreign Application Priority Data

Sep. 23, 1998 (EP) ............................................. 98203204
Jul. 23, 1999 (EP) ............................................. 99202442

(51) Int. Cl.$^7$ ............................................. C07C 67/02
(52) U.S. Cl. ....................................................... 560/263
(58) Field of Search ......................................... 560/263

(56) References Cited

U.S. PATENT DOCUMENTS

| | | | |
|---|---|---|---|
| 3,075,999 A | 1/1963 | June et al. ................ 260/348.6 |
| 3,142,686 A | * 7/1964 | Kreps et al. | |
| 3,178,454 A | 4/1965 | Kloos et al. ............. 260/348.6 |
| 3,275,583 A | 9/1966 | Kloos ............................ 260/22 |
| 3,397,176 A | 8/1968 | Drost ............................. 260/47 |
| 3,953,479 A | 4/1976 | Force et al. ............. 260/348 A |
| 5,245,057 A | 9/1993 | Shirtum ........................ 549/517 |
| 5,278,260 A | 1/1994 | Schaffner et al. ........... 525/507 |
| 5,880,297 A | 3/1999 | Ryan et al. .................. 549/541 |

FOREIGN PATENT DOCUMENTS

| | | | |
|---|---|---|---|
| DE | 3345248 | 6/1985 | .......... C07D/303/48 |
| EP | 0396203 A2 | 5/1990 | ............ C08G/59/32 |
| EP | 0452265 A2 | 4/1991 | ............ C08G/59/06 |
| JP | 50-76012 | 11/1973 | ............ C07C/67/00 |
| JP | 50-95216 | 12/1973 | .......... C07D/303/16 |
| WO | WO 97/44335 | 11/1997 | .......... C07D/301/32 |

* cited by examiner

*Primary Examiner*—Paul J. Killos
*Assistant Examiner*—John N. Calve

(57) ABSTRACT

A process for the manufacture of glycidylesters of branched monocarboxylic acids, comprising (a) the reaction of the α-branched monocarboxylic acid with a halo substituted monoepoxide such as an epihalohydrin (e.g. epichlorohydrin), in a 2–20 molar excess, in the presence of water and a water-miscible solvent as solvent, and in the presence of a catalyst, in an amount of at most 45 mol % of the molar amount of the monocarboxylic acid groups, and preferably at most 30 mol % at a temperature in the range of from 50 to 110, during a period in the range of from 0.8 to 2.5 hr, (b) addition of additional alkali metal hydroxide or alkali metal alkanolate up to about an equimolar amount as to the monocarboxylic acid and reaction at a temperature of from 40 to 80° C., (c) distillation of the obtained reaction mixture to remove the excess halo substituted monoepoxide and the solvent and water formed, and (d) removal of the alkali metal halide salt, in order to complete the dehydrohalogenation (and preferably a dehydrochlorination).

13 Claims, No Drawings

PROCESS FOR THE PREPARATION OF GLYCIDYLESTERS OF BRANCHED CARBOXYLIC ACIDS

The present invention relates to a process for the preparation of glycidylesters of branched monocarboxylic acids.

More in particular the present invention relates to a multistep process for the preparation of glycidylesters of α-branched monocarboxylic acids containing from 5 to 20 carbon atoms and preferably from 9 to 13 carbon atoms.

Glycidylesters of α-branched monocarboxylic acids are useful for the preparation of epoxy, acrylic polyester and alkyd resins, either directly or via intermediate products such as adducts with (meth)acrylic acid amines, polyols and polyacids or as reactive diluents for the preparation of thermoset acrylic, epoxy polyester and/or urethane paints and coatings.

Of particular interest are glycidylesters of aliphatic monocarboxylic acids represented by the formula

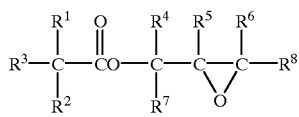

wherein $R^1$, $R^2$ and $R^3$ each represent the same or different alkyl radicals of normal or branched structure containing 1–20 carbon atoms, and $R^4$ through $R^8$ each represent hydrogen or a hydrocarbyl group containing 1–3 carbon atoms. A more preferred product is one where $R^1$ through $R^3$ are alkyl groups containing a sum total of 3–20 carbon atoms and where $R^4$ through $R^8$ are each hydrogen, e.g. the reaction product of neodecanoic acid ($R^1+R^2+R^3=C_8$) and epichlorohydrin.

Glycidylesters of this general type and their method of preparation are disclosed in U.S. Pat. Nos. 3,075,999, 3,178,454, 3,275,583 and 3,397,176, the complete disclosures of each of which are incorporated herein by reference.

Such glycidylesters can be made by reacting an alkali salt of the carboxylic acid with a halo-substituted monoepoxide such as an epihalohydrin, e.g., epichlorohydrin (1–20 molar excess). The mixture is heated (50–150° C.) in the presence of a catalyst forming glycidylester plus alkali salt and water. The water and excess epihalohydrin are removed by azeotropic distillation, and the salt by-product, e.g., NaCl, is removed by filtration and/or washing. The glycidylesters can also be made by reacting the carboxylic acid directly with epichlorohydrin under similar process conditions. The chlorohydrin ester intermediate formed during this reaction is subsequently treated with an alkaline material, e.g., sodium or potassium hydroxide, which yields the desired glycidylester. By-product salt is removed by washing and/or filtration, and water is removed by drying.

Investigations of these reactions have revealed that several heavier by-products are produced during the reactions to varying degrees, and that species which add colour to the main product are contained within the heavier by-products. The heavier by-products include the reaction products of the glycidylester product and/or the chlorohydrin ester intermediate with either unreacted epichlorohydrin, unreacted monocarboxylic acid or salt and/or water at various stages of the synthesis process, and have been depicted hereinafter:

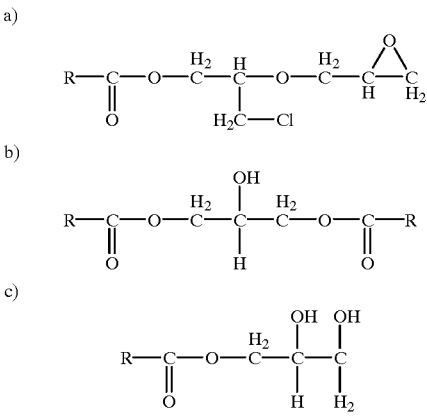

The heavier by-products may also include further reaction products of initially formed compounds with the glycidylester product and other species present. Generally speaking, one or a combination of these or other unidentified heavies are present in the glycidylester reaction product at levels of from 8 wt % to 12 wt %.

Because glycidylesters are thermally and chemically reactive molecules, separation of these by-products from glycidylesters is not easily accomplished. Standard atmospheric distillation techniques have been found to increase the amount of by-products as well as the degree of colour of the esters. It is known that this increase in colour is caused by the reaction at elevated temperatures, as encountered during distillation, of the glycidyl functionality present in the desired product with functionalities present in the by-products, thereby forming additional by-products, which are not separable from the glycidylester and which are extremely sensitive to discoloration upon heating.

One of the remedies for solving this problem of said present by-products, has been disclosed in WO 97/44335.

In said application has been clearly suggested that standard vacuum distillation is ineffective in reducing the initial or aged colour of the glycidylesters and tends to worsen the colour problem.

In said patent application a process for the distillation of the glycidylester reaction product is proposed, which uses a thin film, short pass distillation apparatus and provides a light fraction which after recovery shows a Pt-Co colour value of less than 100 after 20 days storage in contact with air at 125° C. when measured according to ASTM D1209.

Although said distillation process has provided glycidylesters of branched chain saturated monocarboxylic acids, showing an significantly reduced initial colour and a improved colour stability after periods of storage, it will be appreciated that such distillation process will cause a significant cost price increase of the final product, since the reported purity increases are only achieved by discarding about 8% of the intake for obtaining a 96% pure product and up to 30% of the intake for obtaining a 99% pure product. Moreover, said process leads to significant production of chlorinated waste, which is disadvantageous from an environmental point of view It will be appreciated that there is still a need for an improved manufacturing process for glycidylesters of branched monocarboxylic acids, which may lead to the purity and/or colour performance of the product aimed at but at a lower cost price.

As object of the present invention therefor is to provide a process for the manufacture of glycidylesters of branched monocarboxylic acids, with improved initial colour, heat stability and colour stability and/or higher purity, which must be reached at a reduced cost price per product unit.

As a result of extensive research and experimentation, such a process has been surprisingly found now.

Accordingly, the invention relates to a process for the manufacture of glycidylesters of α-branched monocarboxylic acids, comprising (a) the reaction of the α-branched monocarboxylic acid with a halo substituted monoepoxide such as an epihalohydrin (e.g. epichlorohydrin) in a 2–20 molar excess and preferably 3–20, optionally in the presence of water and water-miscible solvent and preferably an aqueous alkanol as solvent, and in the presence of a catalyst in an amount of at most 45 mol % of the molar amount of the monocarboxylic acid, and preferably at most 20% and more preferably of at most 10%, at a temperature in the range of from 30 to 110 (and preferably from 65 to 95° C.), during a period in the range of from 0.5 to 2.5 hr, (b) addition of additional alkali metal hydroxide or alkali metal alkanolate up to a total molar ratio as to the monocarboxylic acid in the range of from 0.9:1 to 1.2:1 and preferably from 0.95:1 to 1.10:1 and reaction at a temperature of from 0 to 80° C. (and preferably from 20 to 70° C.), (c) distillation of the obtained reaction mixture to remove the excess halo substituted monoepoxide and the solvent and water formed, and (d) removal of alkali metal halide salt, e.g. by washing the obtained glycidylester with water, after optionally treating the residual product with a concentrated aqueous alkali metal hydroxide solution, in order to complete the dehydrohalogenation (and preferably a dehydrochlorination).

It will be appreciated that the glycidylester obtained after step (d), can be dried in addition e.g. by distillation or treating with water absorbers.

The process according to the present invention can be carried out either as batch process or as a continuous process. The process preferably uses saturated α-branched monocarboxylic acid.

The preferred reaction time in step (a) is in the range of from 0.9 to 1.5 hours.

The catalyst to be used in step (a) may be selected from alkalimetal hydroxides, alkalimetal carbonates, alkaline earth hydroxides, alkalimetal or alkaline earth metal alcoholates of the formula $X^{n+}(OR^-)_n$, wherein X represents the alkali metal or alkaline earth metal ion and R represents $C_1$–$C_{12}$ alkyl, n represents the valence of the metal ion, or ammonium salts and in particular hydroxides or halides of the formula $R_1R_2R_3R_4N^\oplus Y^-$, wherein $R_1$, $R_2$ and $R_3$ independently of each other may represent an alkyl group having from 1 to 16 carbon atoms, which optionally may be substituted with one or more hydroxyl groups, wherein $R_4$ represents an alkyl group having from 1 to 16 carbon atoms, phenyl or benzyl, and wherein Y represents hydroxyl or halogen.

Another suitable group of basic catalysts for step (a) is formed by phosphonium halides of the formula $R_5R_6R_7R_8P^\oplus Z^-$, wherein $R_5$, $R_6$, $R_7$ and $R_8$ independent of each other may represent monovalent hydrocarbon groups. Preferably $R_5$, $R_6$ and $R_7$ are alkyl, cycloalkyl, aryl, aralkyl, having at most 25 C-atoms and more preferably having at most 18 C-atoms, such as phenyl, butyl, octyl, lauryl, hexadecyl or cyclohexyl. $R_8$ is preferably an alkyl group of from 1 to 10 C-atoms and more preferably of from 1 to 4 and wherein Z is a halogen, such as chlorine, bromine or iodine.

Alkalimetal hydroxides and alkali metal alkanolates having from 1 to 6 carbon atoms are most preferred as catalyst in step (a).

The alkalimetal hydroxide which is used in step (a) may be selected from sodium hydroxide, potassium hydroxide, lithium hydroxide, rubidium hydroxide, and cesium hydroxide, of which sodium hydroxide or potassium hydroxide is more preferred. It will be appreciated that in step (b) only relatively strong and water-soluble metal hydroxides or metal alcoholates have to be used, whereas weaker, less water-soluble metal hydroxides or carbonates are less preferred.

It will be appreciated that the specified molar ratios in step (b) will be constituted by additions of alkali metal hydroxides or alkali metal alkanoates on both steps (a) and (b).

With the term "distillation" used in step (c) is meant removal of the light fractions from the initially obtained reaction mixture (which is indicated in the art as "topping").

In addition, according to a preferred embodiment of the present invention the brine formed in step (a) can be completely or partially removed before entering step (b).

The alkali metal hydroxide or alkali metal alkanolate which is used in steps (b) and (d) are preferably selected from sodium hydroxide, sodium alkanolate having from 1 to 6 carbon atoms, such as sodium isopropanolate, lithium hydroxide or lithium alcoholate. Most preferably sodium hydroxide or sodium alkanolate having from 1 to 6 carbon atoms is used.

Preferably for step (b) sodium hydroxide is used in an aqueous solution of a concentration of from 15 to 60% by weight and more preferably from 20 to 50% by weight.

It will be appreciated that according to the process of the present invention a drying step can take place after the washing in step (d), if desired.

Usually mixtures of glycidylesters of branched monocarboxylic acids are produced, when starting from technical grades of commercially available compositions of α-branched monocarboxylic isomers, such as neodecanoic acids, 2-ethyl hexanoic acid or VERSATIC 9 or 10 or 13 acids (VERSATIC is a trademark) as starting materials.

Preferably VERSATIC acids having 9 to 11 carbon atoms are used as starting material.

It will be appreciated that according to the more preferred embodiments of the process of the present invention step (d) will be carried as anhydrous as possible, i.e. using highly concentrated sodium hydroxide solutions e.g. up to 55 wt %.

It has surprisingly been found, that the process of the present invention can provide very pure glycidylesters of branched monocarboxylic acid, i.e. showing contents of heavier byproducts less than 6 wt % and preferably less than 5 wt % and more preferably less than 4 wt %, which show the desired reduced initial colour, the improved colour stability after periods of storage, and which do not need tailing by distillation for purification, while the process can be further characterized by a very high conversion and selectivity of the halo substituted epoxide with reference to the desired glycidylester.

More in particular it could not be expected by a person skilled in the art that the presence of a base in steps (b) and (d) does not significantly hydrolize the present, just formed glycidylester.

It will be appreciated that preferably an alkanol will be used which enables the dissolution of a sufficient amount of base into the organic phase, whereas on the other hand the total water content in the reaction mixture of step (a) is to be kept in the range of from 4 to 13 mol/mol acid.

With the term "alkanol" as used throughout this specification is meant mono-alkanol as well as polyalkanols such as glycols.

Isopropylalcohol has been found to be most preferred.

The process of the present invention is more preferably carried out, starting from VERSATIC acids, containing from 5 to 13 carbon atoms, and most preferably from 9 to 11 carbon atoms.

It has been found that the water content in step (d) should be as low as possible to avoid hydrolysis of the glycidylesters to be formed. Preferably a highly concentrated aqueous solution of alkali metal hydroxide is used in step (d).

For the same reason the hydrolysable chlorine content after step (b) should be minimized (<2500 mg/kg). A too high level can be reduced by known methods such as an increase of the amount of base used or by a reduction of the reaction temperature in step (b).

The following examples and comparative examples are illustrative of the invention, however without restricting its scope to this embodiment.

EXAMPLE 1

Into a 2 liter reactor, provided with a mechanical stirrer, heating jacket and reflux equipment connected to a distillation column, were put as intake

| VERSATIC-10 acid | 330.0 g | (1.92 moles) |
| --- | --- | --- |
| epichlorohydrine | 709.4 g | (7.67 moles) |
| isopropanol | 551.3 g | (9.17 moles) |
| water | 275.5 g | (15.31 moles) |

The mixture was heated to 56° C. and thereafter an aqueous 50 wt % NaOH solution was dosed, such that 31.6 g of NaOH (0.39 moles) had been added within 20 minutes.

The temperature was increased to 84° C. during 45 minutes and the reaction mixture was kept at this temperature for 15 minutes. Subsequently the reaction mixture was cooled down to 50° C. within 5 minutes. At this temperature phase separation took place within 5 minutes, whereafter 170.8 g of the bottom layer were drawn off. Subsequently 255.7 g of an aqueous 24 wt % NaOH solution (1.53 moles) were dosed within 20 minutes, while the temperature was kept on 50° C.

After the alkali dosing the mixture is stirred at 50° C. for 40 minutes.

Thereafter the reaction product was separated into an aqueous phase and an organic phase (382.8 g of aqueous phase and 1613.8 g of organic phase).

The organic phase was distilled until the end conditions 100 mbar and 110° C. and the residue was subsequently freed from ECH by means of steam distillation (end conditions 120° C., 40 mbar). The remainder (449 g) contained about 10 g/kg hdyrolyzable chlorine. This was converted by addition of 15.0 g of an aqueous 50 wt % NaOH solution at 55° C. (i.e. 1.5 moles of NaOH/mole hydrolyzable chlorine).

The mixture was stirred during 60 minutes at 55° C. After 60 minutes 101.1 g of water were added and a phase separation took place after 10 minutes.

After one hour settling 120.5 g of water layer was drawn off.

Subsequently a renewed washing with 101.2 g of water took place. Stirring was continued during 10 minutes and after settling during 10 minutes 102.3 g of water was drawn off.

The organic phase (435.5 g) was subsequently stripped off with steam and was dried (end conditions 120° C., 40 mbar).

Subsequently 420 g of the glycidylester of VERSATIC acid (CARDURA E-10 monomer) was drawn off having a high purity (VERSATIC and CARDURA are trademarks):
EGC: 4210 mmol/kg, purity=96.2% h
hydrolyzable chlorine: 264 mg/kg
total chlorine: 776 mg/kg
colour: 18 Pt/Co (according to ASTM D1209).

EXAMPLES 2–15 AND COMPARATIVE EXAMPLES a–d

The proceedings of example 1 were repeated in examples 2–5, except that variations were made in steps (a) and (b) as indicated.

The proceedings of example 1 were repeated in examples 6–11, except that variations were made in step (a) (and using isopropanol as solvent).

The proceedings of example 1 were repeated in examples 12–13, except that variations were made in step (b) varying the catalyst.

In example 14 steps (a) and (b) were changed as compared to example 1.

In example 15 all steps (a)–(d) have been changed as compared to example 1.

EXAMPLE 2

Into a 250 ml reactor, provided with a mechanical stirrer, heating jacket and reflux equipment connected to a distillation column. Were put as intake for step a:

|  | mol | g |
| --- | --- | --- |
| VERSATIC 10 acid: | 0.25 | 43.1 |
| Epichlorhydrin (ECH): | 1 | 92.5 |
| Isopropanol: | 1.25 | 75 |
| Water | 2.02 | 36.5 |
| 50% NaOH in water: | 0.05 | 4.1 |

The mixture of the four first components was heated to 75° C. and thereafter the NaOH solution was dosed. The temperature was kept at 75° C. for 80 minutes and subsequently the reaction mixture was cooled down to 50° C. within five minutes. At this temperature phase separation took place where after the bottom aqueous phase was drawn off. Subsequently (step b), 0.2 mol of NaOH and 1.367 mol of water were added. After this alkali dosing, the mixture was stirred vigorously at 50° C. for 60 minutes. Thereafter, stirring was stopped and the reaction product was separated into an aqueous phase and an organic phase. The organic phase was distilled until the conditions of 100 mbar and 95° C. 20 ml water was then dosed to the glycidylester containing bottom residue in 20 minutes while keeping the pressure and temperature at their level. The residue was then kept under these conditions for 10 minutes and finally drawn off and analysed. The results are presented hereafter.

EXAMPLE 3

The procedure of example 2 is repeated except that the isopropanol is replaced by 75 g methylproxitol.

EXAMPLE 4

The procedure of example 2 is repeated except that the isopropanol is replaced by 75 g acetone and that step (b) was performed at 70° C. in 95 minutes.

EXAMPLE 5

The procedure of example 2 is repeated except that the isopropanol is replaced by 75 g ethanol and that step (b) was performed at 70° C. in 95 minutes.

Comparative Example a

The procedure of example 2 is repeated except that no isopropanol or other solvent were used.

Comparative Example b

The procedure of example 2 is repeated except that the isopropanol was replaced by 75 g toluene.

|  | Ex. 2 (IPA) | Ex. 3 (MPT) | Ex. 4 (Acetone) | Ex. 5 (Ethanol) | Comp. ex. a (no solvent) | Comp. ex. b (Toluene) |
|---|---|---|---|---|---|---|
| Hydrolysable chlorine mg/kg | 9031 | 9101 | 28805 | 9050 | 52783 | 64877 |
| Epoxy group content mmol/kg | 4177 | 4152 | 3543 | 41127 | 2732 | 2221 |
| EGC corrected for light ends (ECH) mmol/kg | 4037 | 4032 | 3333 | 4069 | 2675 | 2184 |
| Yield based on acid used (%) | 92 | 91 | 76 | 93 | 61 | 50 |

EXAMPLE 6

Into a 250 ml reactor, provided with a mechanical stirrer, heating jacket and reflux equipment connected to a distillation column. Were put as intake for step a:

|  | mol | g |
|---|---|---|
| VERSATIC 10 acid: | 0.25 | 43.1 |
| Epichlorhydrin (ECH): | 1 | 92.5 |
| Isopropanol: | 1.25 | 75 |
| Water | 2.02 | 36.5 |
| 50% NaOH in water: | 0.05 | 4.1 |

The mixture of the four first components was heated to 75° C. and thereafter the NaOH solution was dosed and the temperature was kept at 75° C. The initial VERSATIC 10 acid concentration was about 1000 mmol/kg. The reaction rate was monitored by acid base titration of VERSATIC 10 acid and sodium salt of VERSATIC 10 acid. The remaining salt of VERSATIC 10 acid after 1.5 hours are listed hereinafter.

EXAMPLE 7

The procedure of example 6 is repeated except that the 0.05 mol NaOH are replaced by 0.1 mol of KOH.

EXAMPLE 8

The procedure of example 6 is repeated except that the 0.05 mol NaOH are replaced by 0.05 equivalent CaOH2.

EXAMPLE 9

The procedure of example 6 is repeated except, that the 0.05 mol NaOH are replaced by 0.005 mol tetramethyl ammonium chloride.

EXAMPLE 10

The procedure of example 6 is repeated except that the 0.05 mol NaOH are replaced by 0.005 mol ethyl triphenyl phosphonium iodide.

EXAMPLE 11

The procedure of example 6 is repeated except that the 0.05 mol NaOH are replaced by 0.05 equivalent sodium carbonate.

| Unconverted species after 1.5 hours | Ex. 6 NaOH | Ex. 7 KOH | Ex. 8 CaOH$_2$ | Ex. 9 TeMAC | Ex. 10 ETPPI | Ex. 11 Na$_2$CO$_3$ |
|---|---|---|---|---|---|---|
| VERSATIC 10 Acid (mmol/kg) | 7 | <2 | 680 | 610 | 680 | <2 |
| Formed salt of VERSATIC Acid (mmol/kg) | 12 | 7 | 94 | 12 | 19 | 65 |

EXAMPLE 12

Two batches (step a) were prepared as follows:

Into a 250 ml reactor, provided with a mechanical stirrer, heating jacket and reflux equipment connected to a distillation column. Were put as intake for step a:

|  | mol | g |
|---|---|---|
| VERSATIC 10 Acid: | 0.25 | 43.1 |
| Epichlorhydrin (ECH): | 1.00 | 92.5 |
| Isopropanol: | 1.25 | 75 |
| Water | 2.02 | 38.5 |
| 50% NaOH in water: | 0.05 | 4.1 |

The mixture of the four first components were heated to 75° C. and thereafter the NaOH solution was dosed. The temperature was kept at 75° C. for 80 minutes and subsequently the reaction mixture were cooled down to 50° C. within five minutes. At this temperature phase separation took place where after the bottom aqueous phase were drawn off. The organic phases of the two batches were then mixed to yield 459.6 g mixture HC.

Subsequently, (step b) in the reactor described above, 76.6 g of the HC mixture was heated to 50° C. 0.067 mol of NaOH and 8 g water were added. After this dosing, the mixture was stirred vigorously at 50° C. for 60 minutes. There after, stirring was stopped and the reaction product was separated into an aqueous phase and an organic phase. The aqueous phase was eliminated and the organic phase was distilled until the conditions of 100 mbar and 95° C. 10 ml water was then dosed to the glycidylester containing bottom residue in 20 minutes while keeping the pressure and temperature at their level. The residue was then kept under these conditions for 10 minutes and finally drawn off and analysed.

EXAMPLE 13

The procedure of example 12 is repeated except that 0.067 equivalent CaOH$_2$ was used instead of NaOH.

Comparative Example c

The procedure of example 14 is repeated except that 0.067 equivalent Na$_2$CO$_3$ was used instead of NaOH.

|  | Example 12 NaOH | Example 13 CaOH$_2$ | Comparative example c Na$_2$CO$_3$ |
| --- | --- | --- | --- |
| Hydrolysable chlorine mg/kg | 11621 | 54128 | 102390 |
| Epoxy group content mmol/kg | 4010 | 2478 | 1612 |
| EGC corrected for light ends (ECH) mmol/kg | 3958 | 2476 | 1586 |
| Yield based on acid intake | 90 | 56 | 36 |

Comparative Example d

The procedure of example 2 is repeated except that the VERSATIC Acid 10 is replaced by 0.25 mol n-decanoic acid. Additionally, the temperature of step b was 0° C. during 2.5 hours followed by 18 hours at room temperature.

EXAMPLE 14

The procedure of example 2 is repeated except that the VERSATIC acid 10 is replaced by 0.25 mol 2-ethyl-hexanoic acid. The temperature of step b was 0° C. during 2.5 hours followed by 18 hours at room temperature. Additionally, the organic phase was distilled until the conditions of 120 mbar and 95° C. 40 ml water was then dosed to the glycidylester containing bottom residue in 30 minutes while keeping the pressure and temperature at their level.

|  | Example 2 VERSATIC 10 | Comparative example d n-decanoic acid | Example 14 2-ethyl hexanoic acid |
| --- | --- | --- | --- |
| Hydrolysable chlorine mg/kg | 9031 |  | 5130 |
| Epoxy group content mmol/kg | 4177 |  | 4762 |
| EGC corrected for light ends (ECH) mmol/kg | 4037 | approx. 3500 | 4701 |
| Yield based on acid intake | 92 | approx. 80 | 94 |

EXAMPLE 15

In a reactor, provided with a mechanical stirrer, heating and reflux equipment connected to a distillation column. Were put as intake in the following proportions:

|  | mol |
| --- | --- |
| VERSATIC 10 Acid | 1 |
| Epichlorhydrin (ECH) | 4.04 |
| Isopropanol | 3.65 |
| Glycidol* | 0.049 |
| Isopropyl glycidyl ether* | 0.063 |
| Water | 9.93 |
| NaOH (50% in water) | 1.016 |

(* Glycidol and isopropyl glycidylether are by-products which may be recycled in eventual recycle streams of the process.)

The mixture of the six first components heated to 42° C. and thereafter the 20% of the NaOH solution was dosed (step a) in 20 minutes and the reactor temperature was increased to 76° C. in 120 minutes.

Subsequently, the reaction mixture was cooled down to 50° C. and the remainder of the NaOH was added in 2 hours (step b). After this alkali dosing, the mixture was kept at 50° C. for 35 minutes. Thereafter, stirring was stopped and the reaction product was separated into an aqueous phase and an organic phase.

The organic phase was then distilled until the conditions of 100 mbar and 114° C. to remove the isopropanol and part of the ECH of the mixture. This was followed by a steam stripping step and a nitrogen stripping to remove the remainder of the ECH and water. (The glycidol contained in the latter distillate stream was removed by phase separation and the distillate organic streams were then recycled for the next batch).

A so-called after-dehydrochlorination step was then performed at 54° C. using 0.075 mol NaOH per mol VERSATIC 10 Acid intake and the reaction time was 60 minute. This was followed by 2 wash step with water and a distillation step with first water and then nitrogen.

The properties of the end product were compared with commercially available glycidylesters:

|  | Example 15 | CARDURA E 10 | GLYDEXX N 10 |
| --- | --- | --- | --- |
| EGC (mmol/kg) | 4225 | 3940 | 3955 |
| Diester* content (%) | 0.94 | 2.8 | 5.3 |
| Colour (Pt/Co, ASTM 1209) | 29.1 | 51 | 25.1 |
| Colour after 20 days at 125° C.** | 463 | 1290 | 1121 |

*Diesters are the adducts of glycidyl ester and its acid.
**Samples were in glass bottles half full with air and the colour was monitored at regular interval.
GLYDEXX is a trademark.

EXAMPLES 16 AND 17

A sample of glycidylester prepared according to example 15 hereafter called CARDURA E10P Monomer was compared with commercial CARDURA E10 Monomer:

A. Cardura E10P Based Adducts With Acrylic Acid (ACE-adduct) And Methacrylic Acid (MACE-adduct)

The adducts of CARDURA Monomers with acrylic acid (ACE-adduct) and with methacrylic acid (MACE-adduct) are acrylic monomers that can be used to formulate hydroxyl functional (meth)acrylic polymers. In order to compensate for the higher Epoxy Group Content of CARDURA E10P Monomer compared to CARDURA E10 Monomer, the amount of (meth)acrylic acid is increased to maintain equimolarity. The use of CARDURA E10P Monomer reduces the reaction time and the colour of the resulting adducts.

|  | Using CARDURA E10 (parts by weight) | Using CARDURA E10P (parts by weight) |
| --- | --- | --- |
| Manufacturing procedure | | |
| Initial reactor charge | | |
| CARDURA Monomer | 250.00 | 250.00 |
| Acrylic acid | 70.93 | 75.06 |

-continued

|  | Using CARDURA E10 (parts by weight) | Using CARDURA E10P (parts by weight) |
|---|---|---|
| Radical Inhibitor | | |
| 4-Methoxy phenol | 0.463 | 0.463 |
| Catalyst | | |
| DABCO T9 (0.07 wt % on CARDURA) | 0.175 | 0.175 |

Compositions of the MACE-adduct

|  | Using CARDURA E10 (parts by weight) | Using CARDURA E10P (parts by weight) |
|---|---|---|
| Initial reactor charge | | |
| CARDURA Monomer | 250.00 | 250.00 |
| Methacrylic acid | 84.73 | 89.68 |
| Radical Inhibitor | | |
| 4-Methoxy phenol | 0.463 | 0.463 |
| Catalyst | | |
| DABCO T9 (0.07 wt % on CARDURA) | 0.175 | 0.175 |

Equimolar amounts of CARDURA Monomer and (meth) acrylic acid, together with the DABCO T9 and 4-Methoxy phenol (185 ppm calculated on CARDURA Monomer weight), are charged to the reactor.

The reaction is performed under air flow (in order to recycle the radical inhibitor).

The reactor charge is heated slowly under constant stirring to about 80° C., where an exothermic reaction starts, increasing the temperature to about 100° C.

The temperature of 100° C. is maintained, until an Epoxy Group Content below 30 meq/kg is reached. The reaction mixture is cooled to room temperature.

|  | Using CARDURA E10 | Using CARDURA E10P |
|---|---|---|
| ACE-adduct characteristics | | |
| Reaction time [min] | 94 | 76 |
| Colour [Pt/Co] | 148 | 42 |
| Viscosity [mPa · s] | 172 | 178 |
| Final acid value [mg KOH/g] | 3.5 | 3.5 |
| Final Epoxy Group Content [meq/kg] | 20.0 | 11.0 |
| Tg of homo-polymer (DSC, midpoint, [° C.]a) | 0 | 0 |
| MACE-adduct characteristics | | |
| Reaction time [min] | 240 | 175 |
| Colour [Pt/Co] | 235 | 37 |
| Viscosity [mPa · s] | 151 | 152 |
| Final acid value [mg KOH/g] | 6.6 | 5.4 |
| Final Epoxy Group Content [meq/kg] | 30.0 | 25.0 |
| Tg of homo-polymer (DSC, midpoint, [° C.]a) | 28 | 28 |

B. The Use of Cardura E10P in Medium Solids Acrylic Polymers For Automotive Refinish Clear Coats Manufacturing procedure Compositions of acrylic polymers CARDURA

|  | Using CARDURA E10 (parts by weight) | Using CARDURA E10P (parts by weight) |
|---|---|---|
| Initial reactor charge | | |
| CARDURA Monomer | 164.40 | 164.40 |
| Xylene | 147.84 | 147.84 |
| Monomer mixture | | |
| Acrylic acid | 46.64 | 49.36 |
| Butyl acrylate | 51.54 | 48.82 |
| Hydroxypropyl methacrylate | — | — |
| Hydroxyethyl methacrylate | 27.20 | 27.20 |
| Styrene | 177.41 | 177.41 |
| Methyl methacrylate | 124.19 | 124.19 |
| Initiator | | |
| Di-tert.-butyl peroxide | 8.87 | 8.87 |
| Post addition | | |
| Di-tert.-butyl peroxide | 5.91 | 5.91 |
| Solvent (to dilute to about 60% solids) | | |
| Butyl acetate | 246.00 | 246.00 |
| Total | 1000.00 | 1000.00 |

The reactor is flushed with nitrogen, and the initial reactor charge heated to 140° C.

The monomer mixture including the initiator is gradually added to the reactor via a pump over 4 hours at this temperature.

Additional initiator is fed into the reactor during another period of 2 hours at 140° C.

Finally the polymer is cooled down and diluted to a solids content of about 60% with butylacetate.

Characteristics of polymers

|  | Using CARDURA E10 | Using CARDURA E10P |
|---|---|---|
| Polymer properties | | |
| Hydroxyl content [% m/m] | 2.46 | 2.57 |
| Mw | 17400 | 17000 |
| Mw/Mn | 2.18 | 2.28 |
| Final Acid Value [mg KOH/g solids] | 4.8 | 6.6 |
| Tg [° C.] | 40 | 40 |
| Solution properties | | |
| Viscosity [mPa.s] | 3275 | 3680 |
| Solids content [% m/m] | 61.8 | 60.8 |
| Colour [Pt/Co] | 20.8 | 13.9 |

C. The Use of Cardura E10P Monomer in Polyester LR-32

Polyester LR-32, with a high hydroxyl content cross-links at low temperature (<80° C.) with aliphatic or aromatic poly-isocyanates.

The amount of CARDURA E10P Monomer used in the polyester preparation is slightly reduced compared with CARDURA E10 Monomer to compensate for its higher EGC. In order to obtain consistent molecular weight and viscosity when using CARDURA E10P Monomer, a small percentage of isophthalic acid is replaced by benzoic acid as chain regulator.

A significant reduction in the colour is observed when the polyester is prepared with CARDURA E10P Monomer.

Manufacturing procedure

Compositions of polyester LR-32

|  | Using CARDURA E10 (parts by weight) | Using CARDURA E10P (parts by weight) |
| --- | --- | --- |
| One stage process |  |  |
| Isophthalic acid | 416.3 | 407.4 |
| Benzoic acid | — | 8.9 |
| Trimethylol propane | 201.6 | 201.6 |
| CARDURA | 382.1 | 361.0 |
| Total | 1000.0 | 978.9 |

Charge the three ingredients to the reactor which is purged with a nitrogen stream. Add 5 parts by weight of xylene. Heat the reactor charge to 240° C. An exotherm starts around 150° C. which will raise the temperature above 200° C.

Heat the reactor to 240° C. and maintain this temperature until an acid value of 6–8 mg KOH/g resin is obtained, which requires approximately 3 hours.

The reaction is stopped and the resin is diluted with xylene to a solids content of 65%.

|  | Using CARDURA E10 | Using CARDURA E10P |
| --- | --- | --- |
| Solution properties |  |  |
| Solids content [% m/m] | 64.4 | 64.5 |
| Viscosity [mPa.s] | 2290 | 2330 |
| Colour [Pt/Co] | 53 | 25 |
| Resin (100%) properties |  |  |
| Acid value [mg KOH/g] | 7.6 | 8.5 |
| Hydroxyl value, theoretical, [eq/kg] | 3.04 | 3.038 |
| Mw | 4060 | 3480 |
| Mw/Mn | 2.38 | 2.13 |

We claim:

1. A process for the manufacture of glycidylesters of α-branched monocarboxylic acids, comprising the steps of:
   (a) reacting an α-branched monocarboxylic acid with an epihalohydrin, in a 2–20 molar excess, in the presence of water present in an amount ranging from 4 to 13 moles per mole of said monocarboxylic acid, and a water-miscible solvent, and in the presence of a catalyst, in an amount of at most 45 mol % of the molar amount of the monocarboxylic acid, at a temperature in the range of from 30 to 110° C., during a period in the range of from 0.5 to 2.5 hr thereby producing a mixture;
   (b) adding to the mixture alkali metal hydroxide or alkali metal alkanolate up to a molar ratio in the range of from 0.9:1 to 1.2:1 as to the monocarboxylic acid groups and reaction at a temperature of from 0 to 80° C. thereby producing a reaction mixture comprising a glycidylester of α-branched monocarboxylic acid, excess epihalohydrin, solvent, water, and alkali metal halide salt;
   (c) distilling the reaction mixture to remove the excess epihalohydrin and the solvent and water to produce the distilled reaction mixture, and
   (d) removing the alkali metal halide salt from the distilled reaction mixture thereby producing the purified glycidylesters of α-branched monocarboxylic acid.

2. The process of claim 1 wherein in step (a) the reaction of the α-branched monocarboxylic acid with the epihalohydrin is carried out, in a 2–20 molar excess in the presence of an alkanol and water as solvent, and in the presence of a basic catalyst in an amount of at most 30 mol % of the molar amount of the monocarboxylic acid, at a temperature in the range of from 50 to 100° C., during a period in the range of from 0.8 to 2.5 hr.

3. The process of claim 2 wherein in step (b) alkali metal hydroxide is added up to about an equimolar amount as to the monocarboxylic acid and reaction at a temperature of from 40 to 80° C.

4. The process of claim 1 wherein the basic catalyst to be used in step (a) is an alkali metal hydroxide, alkali metal carbonate, alkali metal bicarbonate or alkali metal alkanolate.

5. The process of claim 4 wherein the basic catalyst is sodium hydroxide or potassium hydroxide.

6. The process of claim 1 wherein in step (b) sodium hydroxide or sodium alkanolate having from 1 to 6 carbon atoms, is used.

7. The process of claim 2 wherein the basic catalyst is present in an amount of about 20 mole of the molar amount of the monocarboxylic acid.

8. The process of claim 1 wherein the reaction in step (a) is carried out at a temperature in the range of from 65 to 95° C. during a period in the range of from 0.9 to 1.5 hr.

9. The process of claim 1 wherein the addition in step (b) is carried out at a temperature from 20 to 70° C.

10. The process of claim 1 wherein the water-miscible solvent is isopropanol.

11. The process of claim 1 wherein the α-branched carboxylic acid is a saturated α-branched carboxylic acid.

12. The process of claim 1 wherein the alkali metal hydroxide or alkali metal alkanolate is added in step (b) up to a molar ratio in the range of from 0.95:1 to 1.10:1 as to the monocarboxylic acid groups.

13. The process of claim 1 wherein the alkali metal salt is removed in step (d) by washing the obtained glycidylester with water, after optionally treating the residual product with a concentrated aqueous alkali metal hydroxide or an alkali metal alcoholate solution.

* * * * *